(12) United States Patent
Sarfaty et al.

(10) Patent No.: US 8,865,076 B2
(45) Date of Patent: Oct. 21, 2014

(54) METHODS FOR DETECTION AND CHARACTERIZATION OF ABNORMAL TISSUE AND CELLS USING AN ELECTRICAL SYSTEM

(71) Applicant: LS Biopath, Inc., Mountain View, CA (US)

(72) Inventors: Moshe Sarfaty, Cupertino, CA (US); Amir Lev, Mountain View, CA (US)

(73) Assignee: LS Biopath, Inc., Mountain View, CA (US)

( * ) Notice: Subject to any disclaimer, the term of this patent is extended or adjusted under 35 U.S.C. 154(b) by 0 days.

(21) Appl. No.: 13/857,081

(22) Filed: Apr. 4, 2013

(65) Prior Publication Data

US 2013/0230883 A1    Sep. 5, 2013

Related U.S. Application Data

(63) Continuation of application No. 12/650,359, filed on Dec. 30, 2009, now Pat. No. 8,437,845, which is a continuation of application No. 12/524,973, filed as application No. PCT/US2008/052671 on Jan. 31, 2008, now Pat. No. 8,417,328.

(60) Provisional application No. 60/898,684, filed on Feb. 1, 2007.

(51) Int. Cl.
*G01N 27/327*    (2006.01)
*A61B 5/053*     (2006.01)
*A61B 5/00*      (2006.01)
*A61B 5/05*      (2006.01)

(52) U.S. Cl.
CPC .............. *G01N 27/327* (2013.01); *A61B 5/418* (2013.01); *A61B 5/0538* (2013.01); *A61B 5/05* (2013.01); *A61B 5/415* (2013.01); *A61B 2562/046* (2013.01); *A61B 5/053* (2013.01); *A61B 2562/0209* (2013.01); *A61B 5/0536* (2013.01)
USPC ....................................... 422/82.02; 600/547

(58) Field of Classification Search
USPC .................................. 600/547; 422/82–82.02
See application file for complete search history.

(56) References Cited

U.S. PATENT DOCUMENTS 4,458,694 A * 7/1984 Sollish et al. ................. 600/547
5,215,088 A * 6/1993 Normann et al. ............. 600/377

(Continued)

FOREIGN PATENT DOCUMENTS

EP    1174093 A1    1/2002
EP    1174093 A1 *  1/2002   ............. A61B 18/14

(Continued)

OTHER PUBLICATIONS

Guo, et al. "Silver Nanoparticles Doped Silica Nanocomposites Coated on an Optical Fiber for Ammonia Sensing". Sensors and Actuators B 123 (2007) 578-582; Available online Nov. 2006.

(Continued)

*Primary Examiner* — Sean Dougherty
*Assistant Examiner* — Michael C Stout
(74) *Attorney, Agent, or Firm* — Shartsis Friese LLP; Cecily Anne O'Regan

(57) ABSTRACT

An apparatus for the diagnosis of a biological sample is disclosed. An embodiments of the apparatus includes a probe, a probe head distally connectable to the probe, the probe head further comprising a plurality of electrode elements thereby forming an electrode array where each electrode element is variably actuatable to apply an electrical signal to the biological sample; an RF signal source for applying the electrical signal to the electrode array; an electrode selector adapted and configured to switch the electrical signal from the RF signal source between the plurality of electrode elements; and a detection circuit for analyzing a dielectric property received from the biological sample. Methods and kits for diagnosing a biological sample are also disclosed.

15 Claims, 9 Drawing Sheets

(56) References Cited

U.S. PATENT DOCUMENTS

| | | | |
|---|---|---|---|
| 5,810,742 A * | 9/1998 | Pearlman | 600/547 |
| 6,008,889 A | 12/1999 | Zeng et al. | |
| 6,055,452 A | 4/2000 | Pearlman | |
| 6,069,689 A | 5/2000 | Zeng et al. | |
| 6,152,143 A * | 11/2000 | Edwards | 128/898 |
| 6,213,998 B1 | 4/2001 | Shen et al. | |
| 6,271,913 B1 | 8/2001 | Jung et al. | |
| 6,308,097 B1 | 10/2001 | Pearlman | |
| 6,421,559 B1 | 7/2002 | Pearlman | |
| 6,522,910 B1 | 2/2003 | Gregory | |
| 6,560,480 B1 | 5/2003 | Nachaliel et al. | |
| 6,678,552 B2 | 1/2004 | Pearlman | |
| 6,721,058 B2 | 4/2004 | Kim et al. | |
| 6,768,921 B2 * | 7/2004 | Organ et al. | 600/547 |
| 6,788,966 B2 * | 9/2004 | Kenan et al. | 600/372 |
| 6,807,444 B2 * | 10/2004 | Tu et al. | 600/547 |
| 6,845,264 B1 | 1/2005 | Skladnev et al. | |
| 6,859,282 B1 | 2/2005 | Callow et al. | |
| 6,928,315 B1 | 8/2005 | Nachaliel | |
| 6,993,383 B2 | 1/2006 | Assenheimer | |
| 7,103,401 B2 | 9/2006 | Schomaker et al. | |
| 7,141,019 B2 | 11/2006 | Pearlman | |
| 7,162,291 B1 | 1/2007 | Nachaliel | |
| 7,419,487 B2 | 9/2008 | Johnson et al. | |
| 7,627,362 B2 * | 12/2009 | Gregory et al. | 600/427 |
| 7,630,759 B2 * | 12/2009 | Davies | 600/547 |
| 7,991,475 B1 * | 8/2011 | Tang et al. | 607/45 |
| 8,010,187 B2 * | 8/2011 | Freed et al. | 600/547 |
| 8,024,022 B2 * | 9/2011 | Schulman et al. | 600/372 |
| 8,121,697 B2 * | 2/2012 | Greenberg et al. | 607/54 |
| 8,417,328 B2 | 4/2013 | Sarfaty et al. | |
| 8,437,845 B2 | 5/2013 | Sarfaty et al. | |
| 2002/0038096 A1 * | 3/2002 | Gregory et al. | 600/547 |
| 2002/0099415 A1 * | 7/2002 | Panescu et al. | 607/24 |
| 2002/0123694 A1 * | 9/2002 | Organ et al. | 600/547 |
| 2002/0138019 A1 * | 9/2002 | Wexler et al. | 600/547 |
| 2002/0183645 A1 | 12/2002 | Nachaliel | |
| 2003/0088189 A1 * | 5/2003 | Tu et al. | 600/549 |
| 2003/0100823 A1 * | 5/2003 | Kipke et al. | 600/378 |
| 2003/0105410 A1 * | 6/2003 | Pearlman | 600/547 |
| 2004/0006264 A1 * | 1/2004 | Mojarradi et al. | 600/378 |
| 2004/0054393 A1 * | 3/2004 | Stemme et al. | 607/149 |
| 2004/0077944 A1 | 4/2004 | Steinberg et al. | |
| 2004/0127780 A1 * | 7/2004 | Ollmar et al. | 600/365 |
| 2004/0152997 A1 * | 8/2004 | Davies | 600/547 |
| 2004/0167421 A1 * | 8/2004 | Gregory et al. | 600/378 |
| 2004/0210158 A1 | 10/2004 | Organ et al. | |
| 2004/0243018 A1 * | 12/2004 | Organ et al. | 600/547 |
| 2005/0004490 A1 * | 1/2005 | Organ et al. | 600/547 |
| 2005/0043726 A1 * | 2/2005 | McHale et al. | 606/27 |
| 2005/0065418 A1 | 3/2005 | Ginor | |
| 2005/0085869 A1 * | 4/2005 | Tehrani et al. | 607/42 |
| 2005/0101876 A1 | 5/2005 | Pearlman | |
| 2005/0137662 A1 * | 6/2005 | Morris et al. | 607/101 |
| 2006/0009814 A1 * | 1/2006 | Schulman | 607/45 |
| 2006/0085049 A1 * | 4/2006 | Cory et al. | 607/48 |
| 2006/0085056 A1 * | 4/2006 | Schouenborg | 607/148 |
| 2006/0172541 A1 * | 8/2006 | Lee | 438/702 |
| 2006/0173359 A1 * | 8/2006 | Lin et al. | 600/478 |
| 2006/0241514 A1 * | 10/2006 | Davies | 600/547 |
| 2007/0067007 A1 * | 3/2007 | Schulman et al. | 607/115 |
| 2007/0135729 A1 * | 6/2007 | Ollmar et al. | 600/547 |
| 2007/0169333 A1 * | 7/2007 | Donoghue et al. | 29/592 |
| 2007/0197892 A1 * | 8/2007 | Shen et al. | 600/378 |
| 2007/0203425 A1 * | 8/2007 | Woo et al. | 600/547 |
| 2007/0233204 A1 * | 10/2007 | Lima et al. | 607/46 |
| 2007/0276286 A1 * | 11/2007 | Miller | 600/564 |
| 2008/0004543 A1 * | 1/2008 | Davies | 600/547 |
| 2008/0009764 A1 * | 1/2008 | Davies | 600/547 |
| 2008/0076998 A1 * | 3/2008 | Organ et al. | 600/372 |
| 2008/0138581 A1 * | 6/2008 | Bhandari et al. | 428/156 |
| 2008/0160635 A1 * | 7/2008 | Castro et al. | 436/501 |
| 2008/0221475 A1 * | 9/2008 | Gregory et al. | 600/547 |
| 2008/0281314 A1 | 11/2008 | Johnson et al. | |
| 2009/0076497 A1 * | 3/2009 | Morris et al. | 606/41 |
| 2009/0253193 A1 | 10/2009 | Gregory | |
| 2009/0264791 A1 | 10/2009 | Gregory et al. | |
| 2009/0306535 A1 * | 12/2009 | Davies et al. | 600/547 |
| 2010/0069776 A1 * | 3/2010 | Greger et al. | 600/544 |
| 2010/0106047 A1 * | 4/2010 | Sarfaty et al. | 600/547 |
| 2010/0121173 A1 * | 5/2010 | Sarfaty et al. | 600/407 |
| 2010/0256633 A1 * | 10/2010 | Kelly et al. | 606/41 |
| 2011/0082383 A1 * | 4/2011 | Cory et al. | 600/547 |
| 2011/0125001 A1 * | 5/2011 | Fang et al. | 600/372 |
| 2012/0138335 A1 * | 6/2012 | Tathireddy et al. | 174/250 |

FOREIGN PATENT DOCUMENTS

| | | |
|---|---|---|
| JP | 2001238862 A2 | 9/2001 |
| WO | WO0152731 A1 | 7/2001 |
| WO | WO0232335 A1 | 4/2002 |
| WO | WO2005110218 A1 | 11/2005 |
| WO | WO2007017634 A2 | 2/2007 |
| WO | WO2007017634 A3 | 2/2007 |
| WO | WO2008095075 A1 | 8/2008 |
| WO | WO2008095108 A1 | 8/2008 |
| WO | WO2009001326 A1 | 12/2008 |

OTHER PUBLICATIONS

Filho, Pedro Bertemes "Tissue Characterization using and Impedance Spectroscopy-Probe" Sep. 2002.

"A 30 electrical impedance tomography (EIT) system for breast cancer detection" V Cherepenin et al. Physiological Measurment 22 (2001) 9-18.

Zou, et al. A Review of Electrical Impedance Techniques for Breast Cancer Detection Medical Engineering & Physics, 25 (2003) 79-90 (Oct. 15, 2002).

* cited by examiner

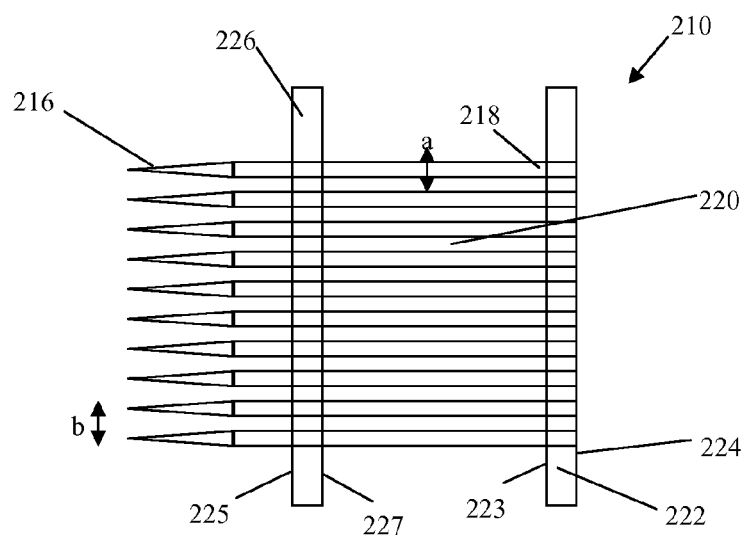
FIG. 2B
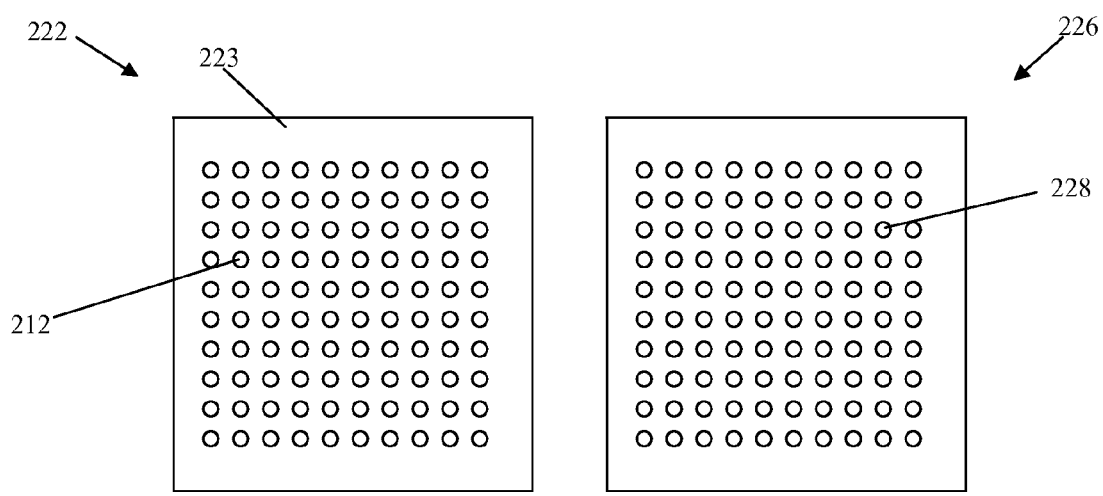
FIG. 2C  FIG. 2D

METHODS FOR DETECTION AND CHARACTERIZATION OF ABNORMAL TISSUE AND CELLS USING AN ELECTRICAL SYSTEM

CROSS-REFERENCE

This application claims priority to U.S. patent application Ser. No. 12/650,359 filed Dec. 30, 2009, which is a continuation of Ser. No. 12/524,973 having a 371(e) filing date of Dec. 30, 2009, which is the U.S. National Stage of PCT/2008/52671 filed Jan. 31, 2008 which claims the benefit of U.S. Provisional Application No. 60/898,684, filed Feb. 1, 2007, entitled "Electrical System for Detection and Characterization of Cancer Cells" which are incorporated herein by reference in their entirety.

BACKGROUND OF THE INVENTION

The invention relates generally to diagnostic methods for real time diagnosis of biological tissue and cells. A diagnosis of abnormal tissue can be made by the detection of differences in properties of biological cells, properties such as cell density, size and composition. A diagnosis of abnormal tissue may also include a characterization of these differences in cellular properties. In addition to aiding a health care provider with making a diagnosis of abnormal tissue, an apparatus for diagnosis that provides real-time imaging ensures that the abnormal tissues is also completely removed during a surgical procedure so that the subject does not have to undergo multiple surgical procedures to remove all traces of the abnormal tissue. Typically it takes 2 to 5 days to obtain a conclusive answer on the surgical success which is determined after detailed pathology and histology analysis is performed on the sample. Real-time imaging would give feedback to the surgeon during the surgery and thereby reducing the possibility that the subject will have to undergo a $2^{nd}$ surgery due to the presence of "positive margins", or not enough cancer-free margins on the excised tissue.

Current devices and methods for detecting abnormal tissue in a sample have several disadvantages. The methods currently used, which include X-rays, ultrasound imaging, magnetic resonance imaging, thermal imaging, radiofrequency (RF) reflection and absorption, and electrical impedance techniques, have the disadvantage that the detection of cellular abnormalities is done by measuring the changes in electrical impedance of the tissue globally rather than locally because current devices and methods are positioned outside of the body when in use. Apparatuses that use global measures are less sensitive. For example, in X-ray imaging the sensitivity of the device in imaging small-size cancer lumps such as lumps that are less than 3 mm in size is low. Additionally, in cases where there is a low relative amount of malignant cells adjacent to benign cells, the sensitivity of the X-ray is less than 30%. X-rays are also affected by any other objects that may absorb the X-rays, such as a tissue or bone located between the X-ray source and the detector. Additionally, an X-rays machine cannot be used inside the body.

Another technique for detecting the presence of abnormal tissue is the use of ultrasound waves to detect cancer cells. Ultrasound machines image tissue by looking at the reflection of the ultrasound waves of the denser cells. Also the elasticity differences between benign and malignant cells contribute to the image produced by ultrasound. The use of ultrasound is further limited in the minimum size of detectable abnormal tissue because ultrasound imaging of smaller sizes is subject to poorer signal to noise ratio. Similarly, it is also difficult to detect changes in cell density of the tissue in denser media.

Another imaging apparatus used to detect the presence of abnormal tissue is the MRI machine. Like the other imaging apparatuses previously mentioned, MRI image is also affected by cell density and composition. Further, the MRI image is strongly affected by the amount of background noise from the overall tissue scanned and is also limited by the size of abnormal tissue that is detectable. And like X-ray, MRI cannot be used inside of the body.

Other imaging methods include: thermal imaging techniques which detect changes in the temperature of tissues that have denser cell densities and which attract more blood flow to the area; RF reflection and absorption is also used to detect cancer cells by detecting variations in the reflection and absorption of RF as compared to benign cells; electrical impedance techniques have also been developed to determine the malignancy of the cells within the organ by monitoring electrical responses from the outer surface of the tissue.

Sometimes a tissue requires further analysis. For example, it may be beneficial to know whether a sample of abnormal cells is benign or malignant. It may, therefore, be necessary to send the sample out for analysis to a pathology lab. In the pathology lab, cancerous cells are characterized using histological methods which are time consuming and may involve complex sample preparation procedures that can last anywhere from 8-12 hours.

Because the current techniques mentioned above are typically capable only of being positioned outside of the body there may be difficulty in detecting small volumes of abnormal tissue or testing small sample areas. Also, positioning the detecting device outside of the body creates the potential for a greater amount of interference with neighboring tissue, makes it more difficult to reach the target tissue through structures in between the target tissue and the testing device, and increase the likelihood that the signal to noise ratio will be poor. In addition, the current methods for detecting abnormal tissue employ bulky machinery. Further, tissue samples are currently sent to pathology labs for testing which ultimately increases the time frame for making a diagnosis.

Thus, there exists a need for devices and methods that detect in real-time the near-field and far-field electrical effects of abnormal tissue with high sensitivity and precision which is capable of being contained in a compact unit that is easily manipulated in reference to the sample. In addition to the advantage that the invention described herein provides real-time diagnosis of the sample being tested, an automated real-time diagnosis instrument will help to eliminate the possibility of human error or missing a critical volume of tissue.

SUMMARY OF THE INVENTION

An aspect of the invention is directed to an apparatus for diagnosing a biological sample. The apparatus comprises a probe; a probe head distally connectable to the probe, the probe head further comprising a plurality of electrode elements forming an electrode array each electrode element variably actuatable to apply an electrical signal to the biological sample; an RF signal source for applying the electrical signal to the electrode array; an electrode selector adapted and configured to switch a current pulse from the RF signal source between the plurality of electrode elements; and a detection circuit for analyzing a dielectric property received from the biological sample. In some configurations the apparatus comprises a plurality of serially deployable probe head each probe head comprising one or more electrodes. The electrode selector adapted and configured to switch between the plurality of electrode elements is typically a multiplexer. The probe heads typically have an electrode array area of less than 100 mm². The apparatus can be configured so that the probe head collects successive groups of current pulses over time. The detection circuit of the apparatus can also be configured to measure the dielectric property of the sample locally and if desired obtain a plurality of measurements in response to a pulsed signal. The dielectric property from the biological sample received by the detection circuit of the device is typically a function of at least one of voltage, current or frequency and is typically analyzed by the apparatus in real-time. The apparatus can be configured so that at least two target parameters values are derived from a target current pulse. In addition, the apparatus can analyze the dielectric properties and, hence, the biological tissues based on those properties. If desired, a processor can be provided for analyzing a group of parameters with reference to a stored parameter. The apparatus can be used to measure the near-field response of the sample. Alternatively, the apparatus can be used to measure the far-field response of the sample. Further, the apparatus described herein can measure both the near-field and the far-field electrical response from the same biological sample, if desired. The near-field electrical response is measured close to the probe heads of the apparatus. The measurement of both near-field and far-field response by the apparatus can cover a wide range of electrical frequencies and/or current/voltage amplitudes to characterize the electrical properties of the sample. In some configurations, the apparatus is adapted to be handheld. In addition, the apparatus can be configured to be used is situ. Alternatively, the apparatus can be adapted and configured to be used with an endoscope. In another embodiment, a metrology unit can also be provided with the device. When a metrology unit is used, the metrology unit scans an extracted biological sample in three dimensions at different locations. An apparatus with a metrology unit can further consist of a motorized stage adapted and configured to receive a mounted biological sample.

Another aspect of the invention is directed to an apparatus for determining surgical efficacy, comprising: a probe adapted and configured to engage a target tissue of a mammal at a surgical site at a distal end of the probe; a probe head distally connectable to the probe, the probe head further comprising an electrode array adapted to apply an electrical signal to the target tissue; an electrode selector adapted and configured to switch the electrical signal between electrodes in the electrode array; and an analyzer for comparing a signal received from the target tissue at the surgical site by one or more collection elements with a reference signal from a benign tissue sample. In some configurations the apparatus comprises a plurality of serially deployable probe heads each probe head comprising one or more electrodes. The probe head typically has an electrode array area of less than 100 mm² Additionally the apparatus may further comprise an RF signal source for applying the electrical signal to the electrode array. The electrode selector adapted and configured to switch the electrical signal from the RF signal source between a plurality of electrode elements is typically a multiplexer. The detection circuit of the apparatus may further detect a dielectric property received from the target tissue. The detection circuit can, if desired, obtain a plurality of measurements in response to a pulsed signal. Additionally, the apparatus can further comprise a processor for analyzing a group of parameters with reference to a stored parameter. The apparatus described herein may be configured so that the probe head collects successive groups of pulsed signals over time. Furthermore, at least two parameter values may be derived from a target current pulse. The detection circuit of the apparatus can be configured to measure the dielectric property locally. The dielectric property from the biological sample received by the detection circuit of the device is typically a function of at least one of voltage, current or frequency and is typically analyzed by the apparatus in real-time. In addition, the apparatus can analyze the dielectric properties and model the biological tissues based on those properties. The apparatus described herein can further be capable of measuring both the near-field or far-field electrical response from the same biological sample, if desired. Alternatively, the apparatus can measure the near-field response in the sample or it can measure the far-field response in the sample. The near-field electrical response is measured close to the probe heads of the apparatus. The measurement of both near-field and far-field response can cover a wide range of electrical frequencies and/or current/voltage amplitudes to characterize the electrical properties of the sample. In some configurations, the apparatus is adapted to be handheld. In addition, the apparatus can be configured to be used is situ. Alternatively, the apparatus can be adapted and configured to be used with an endoscope. In another embodiment, a metrology unit can also be provided with the device. When a metrology unit is used, the metrology unit scans an extracted biological sample in three dimensions at different locations. An apparatus with a metrology unit can further consist of a motorized stage adapted and configured to receive a mounted biological sample.

Also described herein is a method for diagnosing a biological tissue. The method of diagnosing comprises engaging the biological tissue with a probe, the probe having a probe head distally connectable to the probe, the probe head further comprising at least a plurality of electrode elements in an array for applying an electrical signal to the biological tissue of a mammal; an RF signal source for applying the electrical signal to the electrode array; an electrode selector adapted and configured to switch a current pulse from the RF signal source between the plurality of electrode elements; and a detection circuit for analyzing a first dielectric signal received from the biological tissue; emitting an electrical signal from one or more electrode elements; collecting the first dielectric signal from the biological tissue; analyzing the first dielectric signal received from the biological tissue to produce a result; and diagnosing the biological tissue based on the result. The method may further comprise applying the probe to a tissue site with a body of the mammal. Alternatively, the method may further comprise approaching the tissue site within the body of the mammal with the probe. Another alternative of the method further comprises inserting the probe into a body of the mammal through an endoscope. The method for diagnosing may also comprise the steps of replacing the probe head with a second probe head and thereafter emitting an electrical signal; collecting a second dielectric signal from the biological tissue; analyzing the second dielectric signal received from the biological tissue to produce a result; and diagnosing the biological tissue based on the result. The first dielectric signal and the second dielectric signal may be the same signal. The analyzing step of the method described herein consists of analyzing the signal in real-time. Additionally, the method of diagnosing further comprises the step of comparing the signal received from the biological tissue to a signal of a reference sample. The reference sample could be a benign tissue sample and the benign tissue sample could be obtained from the same mammal as the sample.

Also contemplated is a kit for diagnosing a biological tissue comprising: a probe; and a probe head adapted and configured for use with the probe, the probe head comprising at least a plurality of electrode elements in an array adapted to apply an electrical signal to a biological tissue. The kit typically comprises an electrode selector adapted to select at least one active electrode element. The kit may further comprise a plurality of probe head connectable to the probe. Additionally, the kit may further comprise a console, wherein the console further comprises a computer and a monitor. The console may further comprise a base and when present, the probe may be adapted to be connected to the base through a connection. The connection may be a wire connection or the connection may be a wireless connection. The wireless connection further is an operating room approved wireless connection. The results are typically displayed on the monitor

INCORPORATION BY REFERENCE

All publications, patents, and patent applications mentioned in this specification are incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 2B-H illustrates front views and cross-sectional views of the components of the electrode array.

DETAILED DESCRIPTION OF THE INVENTION

Figure 1:
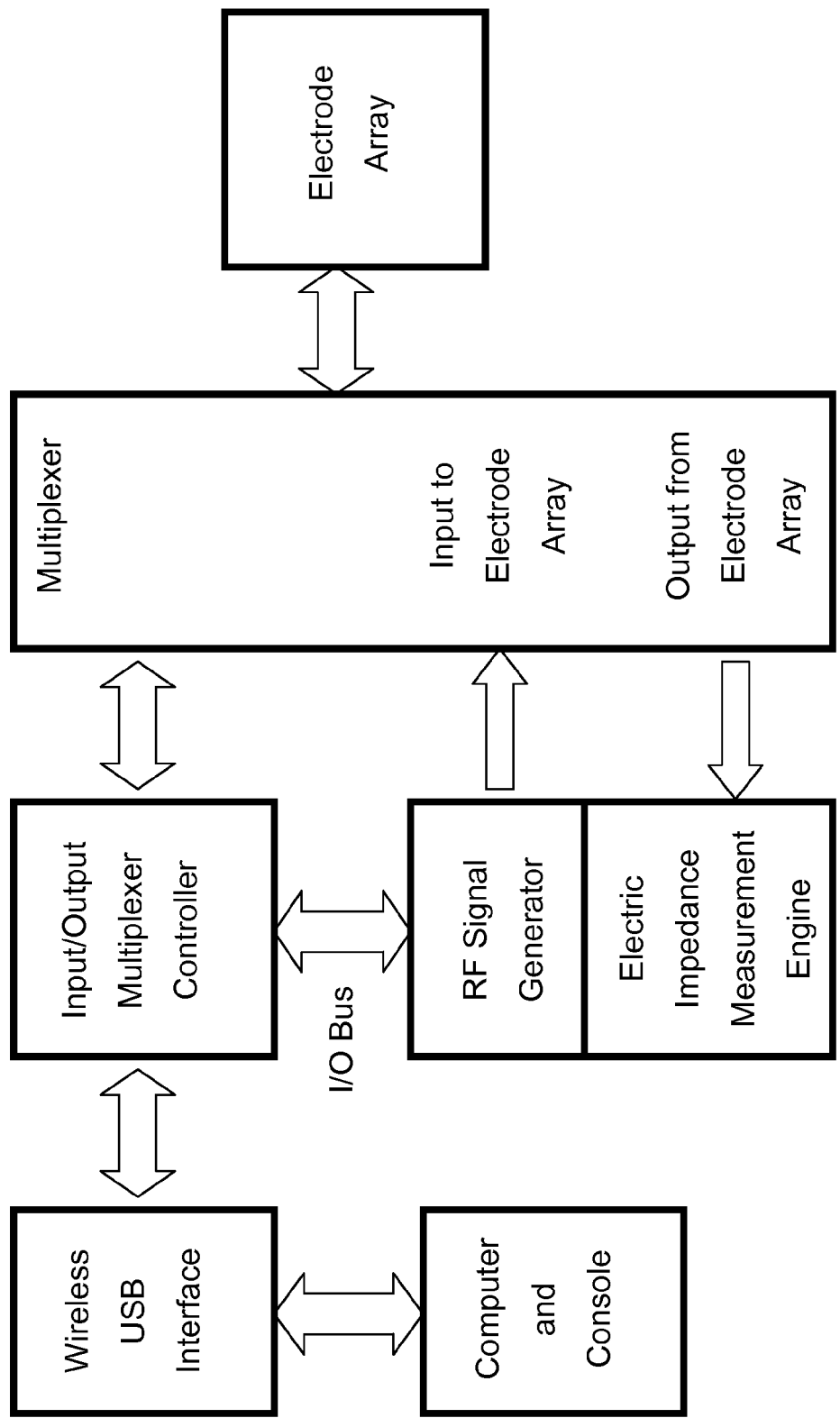
FIG. 1 is a block diagram of the components of the electrical system.

The devices, apparatuses, methods, and kits described herein are adapted and configure to rapidly determine the spatial location of abnormalities in a biological sample, or any soft material that can be probed. The biological sample can come from any mammal or warm blooded animal which can serve as a sample donor. Abnormal tissue and cells includes both malignant and benign tissues and cells. The devices, systems, methods, and kits described are able to discriminate between different types of cells by using near-field and far-field electrical signals of the dielectric properties of the tissue and cells. As an example, in comparison to normal cells, cancer cells tend to be of different size and shape, their nuclei tend to be larger and more prominent, they form more dense collections of cells, they have irregular boundaries, and they vary in chemical composition. These variations may impact the dielectric properties of the cell/ tissue in response to a stimulus. The electrical device described herein utilizes a set of electrodes that measures differences or variations in the dielectric properties of the cells in vitro, in situ, or in vivo, by measuring the electrical response of the cells/tissue while being in close proximity to the cells/tissue. In other words the measurement is a local measurement made. The measurements can be made locally because the electrical measurement device described in this invention utilizes a set of electrodes that are used inside or are inserted into the tissue at the location of interest. The variations in the dielectric properties are detected by measuring parameters of the electrical response of the cells/tissue such as by measuring impedance, capacitance, inductance, or resistance of the electrical circuit, the electric circuit consisting of the selected electrode tips and the biological cells/ tissue between them.

The sample or body can be scanned by placing the probe head in different spatial locations relative to the sample or body. The spatial location of the probe is defined by the user who positions the device in the sample along a desired x- and y-coordinates. The depth that the probe scans is determined by the amount of penetration or intrusion used for the electrodes. Alternatively, the probe head can be positioned automatically using a software program and robotic controller. The surface spatial resolution is determined by the electrode separation in the probe head and the depth resolution is determined by the tip size and the depth the electrodes penetrate the sample. The exposed tip of the electrodes is the conduction portion of the electrode while the remainder of the electrode is electrically isolated the sample and neighboring electrodes by a layer of insulation. From the scan, a three dimensional (3D) map is generated detailing the location of abnormal tissue or cells or "care areas" based on the dielectric properties measured at the different sites in the sample. The mapping of the scan areas provides an accurate and precise 3D map of the cancer margins and can be further used as a guide for additional therapeutic procedures that may be required. The invention described herein can be implemented in both the operating room and in the pathology lab.

The present invention implements real-time diagnosis of abnormal tissue and cells where the detection and characterization of the abnormal tissue and cells can be performed either in-vivo or inside the body, in vitro or outside the body, in situ in the original tissue where the cells are located.

I. DEVICE OVERVIEW

FIG. 1 is a flow diagram of the electrical components of the device. The electrical signal generator or radio frequency (RF) signal generator will generate voltage or current signals of low amplitudes that will not affect the biomaterial. The RF frequency of the signals generated can be scanned at a frequency ranging from as low as a few Hz to hundreds of MHz. The frequency dependence of the tissue can be used to characterize the tissue response. The signal generator can be adjusted by the user to vary the amplitude, phase, frequency, and polarity of the stimulating signal to provide the highest sensitivity and the best differentiation results. The signal from the signal generator will be sent to a multiplexer switching device, or other electrode activating device, that controls which electrodes of the electrode array will be active. The multiplexer, and which electrodes are activated, is controlled by an input/output multiplexer controller. The controller is interfaced with a computer programmed with various algorithms for controlling which electrodes are activated for a desired protocol. Depending on the protocol selected, the computer sends an activating sequence that designates which electrodes to activate and in what order and timing. The controller then controls the multiplexer according to the activating sequence. The active electrodes send an electrical signal stimulus into the sample and detect the dielectric response of the tissue in response to the stimulus. The dielectric signal from sample is then compared to the signal going into the tissue. The signal recorded from the sample can also be compared to a signal generated by a benign reference sample. Abnormalities in the sample will then be determined due variations in the dielectric response as determined from the comparison. A series of measurements can be made at various locations throughout the sample and the responses from the various locations throughout the sample can then be used to identify abnormal tissue, for example, cancer cells. The electrodes, prior to taking a measurement, can be calibrated and the calibrated signal subtracted from the recorded dielectric signal from the suspect sample areas to isolate the signal response of the sample from any ambient electrical noise. The calibration may further includes a measurement from a reference sample of the subjects own normal tissue to characterize a normal tissue response unique to the individual patient and which can be used to detect signal measurements from abnormal tissue.

Once the response from a given area of tissue has been measured, the multiplexer can switch between different sets of electrodes to detect dielectric properties from different regions of the sample. Relevant active electrodes can be selected to measure the near-field effects of the stimulus on the tissue. Electrodes further apart can be selected to measure the far-field effects as well. The regime for either the near-field or the far-field is determined by the ratio of the electrode tip diameter to the gap between the electrodes. Near field effects are measured when the ratio is higher or equal to 1.0. If the ratio is any other value than the far-field effects are measured.

The electrical responses of the sample is then sent to the electric impedance measurement engine by way of the multiplexer. The electric impedance meter is used to measure the electrical properties of the biological sample between pair of electrodes. Capacitance, inductance and resistance can be measured from the bio-electric circuit and the most sensitive responses to changes between benign and malignant cells will be selected. The overall impedance of the circuit, both real and imaginary parts, and the sample response to different frequencies will be used to detect abnormalities. The responses will be gathered from all the electrodes by a console consisting of a computer and monitor and the results displayed on the monitor after data analysis is completed. Variations in the measured response from baseline will be indicated to the operator. As shown in FIG. 1, the console is in two way communication with the multiplexer and multiplexer control unit. The computer can be wired to the multiplexer or, in the alternative, is in electrical communication with the multiplexer through a universal serial bus (USB) interface or wireless connection. Where time is not an issue, the measured response can be recorded using several frequencies, voltages and currents to provide spectral dielectric response that will characterize the tissue, and the suspected areas can then be sent to a pathology lab for further analysis.

Figure 2A:
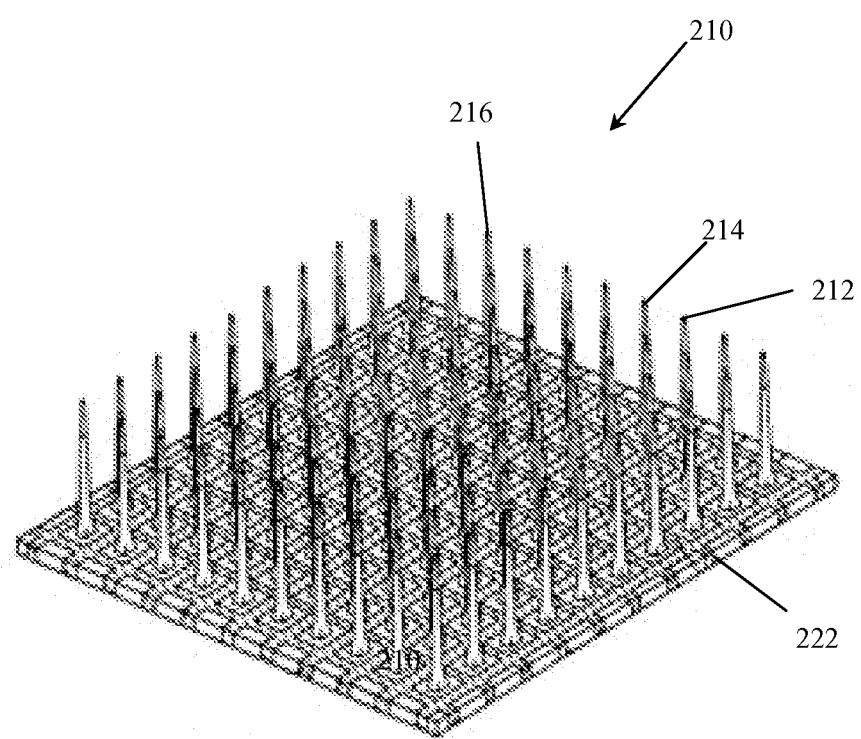
FIG. 2A illustrates a 2D perspective view of the electrical array of the probe head.

Electrophysiology employs the use of either a single electrode or an electrode array to record signals from the target. An electrode array 210 consists of a plurality of electrodes 212 as seen in FIG. 2A. Each electrode 212 is electrically isolated from the adjacent electrode 214 to enable point stimulation and detection of signals from the tissue. An electrode array 210 can consist of any number of electrodes. FIG. 2A illustrates a 10×10 electrode array 210. Typically the electrode array 210 has an area of 100 mm$^2$. In some cases, a larger or smaller electrode array is desired. The electrode array can be as large as 10 cm by 10 cm, or as small as 1 mm$^2$, or any area in between. The electrode array area can be any size necessary to be useful to the user. The electrode array can have the same number of electrodes along the x- and y-axes, as seen in the figure, or the number of electrodes along the x- and y-axes can vary from each other. While FIG. 2A illustrates an electrode array 210 with the electrodes 212 aligned along both the x- and y-axes, it may sometimes be of use to configure the electrodes of the electrode array such that the electrodes are offset with respect to each other. Alternatively, the electrodes may be arranged in other geometric configurations, such as in a circular pattern. The electrodes can be configured in any arrangement or can be spaced in the array based on need, such as based on the sample size, the expected tumor size, the size of the margins, the cancer type and the grade within the sample. The sampling electrode positioning can be optimized physically by the distance and the size of the electrodes in the electrode array and by software that selects the pairing of the active electrodes and the area coverage. In addition to the electrodes being electrically isolated from each other, the holder of the entire electrode array is electrically isolated from nearby structures except where desired, for example, by the wires connecting the individual electrodes to the multiplexer.

FIG. 2B is a cross section of the electrode array 210 shown in FIG. 2A. The electrode array 210 of FIG. 2A consists of a multiple electrodes 212. The electrodes 212 are typically 0.5 mm in diameter, which is indicated by the double sided arrow, a, along the width of the electrode 212. Typically the electrodes are tapered to facilitate insertion of the electrodes into the tissue. In such an embodiment, the diameter of the electrode 212 is widest at the base 218 of the electrode 212. The tips 216 of the electrodes 212 are usually spaced at least 1 mm apart from each other as indicated by double-sided arrow, b. The close proximity of the electrodes allows the dielectric properties to be measured locally through near-field measurements, or measurements of the sample located close to the electrode tips and of relatively small volume. If the ratio between the electrode diameter and the distance between the electrode tips of a given volume is equal to or larger than 1, then the near-field effects of the sample is detected. Measuring the near-field response further allows for greater sensitivity in that it detects individual cell response. Measuring the near-field effects has the additional benefit of improving the signal to noise ratio, and enables the detection of a wider range of electrical frequencies and amplitudes. However, the far-field effects of the sample can also be measured by selecting the appropriate electrodes. The far-field response is the measurement of larger sample volumes located between remote electrodes. If the ratio of the between the electrode diameter and the gap between the electrodes sampling a volume is less than 1 then the far-field effect is being measured. Typically, because the electrode spacing is fixed, the same configuration and volume size is measured throughout the entire scan.

The electrodes 212 of the electrode array 210 can be fabricated using microfabrication techniques known in the art. The electrodes 212 are typically aligned along a fixed plate 222 on which they are fabricated. A front view of the fixed plate 222 of the electrode array 210 is shown in FIG. 2C. The electrodes are fabricated on the proximal side 223 of the fixed plate 222. On the distal side 224 of the fixed plate 222, contact pads (not shown) are in electrical communication with the electrodes 212. The contact pads can then be hard-wired to the multiplexer element (not shown). The fixed plate 222 is typically made out of silicon or any other suitable material for electrically isolating the individual electrodes from each other at their base.

The electrode array can be outfitted to include a moveable plate 226, the front view of which is shown in FIG. 2D. The moveable plate 226 consists of a series of openings 228 which correspond to the position of the electrodes 212 on the fixed plate 222 of FIG. 2C. The moveable plate 226 functions as a stopper to prevent the electrodes 212 from being inserted into the tissue further than desired. In FIG. 2B, only the electrode tips 216 and the portion of the electrode on the proximal side 225 of the moveable plate 226, which is proximal to the tissue, will be inserted into the tissue. The portion of the electrodes 212 on the distal side 227 of the moveable plate 226 will remain outside of the tissue. The moveable plate is slid 216 along the electrode to the desired position to control the depth to which the electrodes are inserted. In embodiments where a moveable plate is used, the moveable plate can be adjusted either manually or automatically. Typically the electrodes are positioned into the sample and the moving plate serves to limit the degree of insertion into the sample. However, the electrical device can further use backside suction to guarantee contact integrity between the electrode array and the sample. The result of backside suction is that the sample is pulled by the suction over the electrodes and towards the moveable plate. Typically suction is applied to the tissue by a vacuum pump connected via tubing, such as plastic tubing, to the probe head. Either the fixed plate or the moveable plate or both plates of the electrode array on the probe head consists of perforations or holes that serve as openings through which the suction force is applied to the tissue. The suction force is applied when the user switches on the vacuum pump.

Figure 2E:
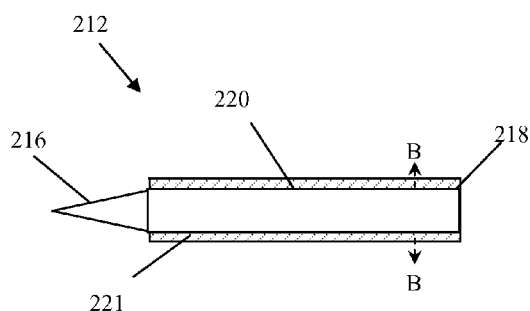

FIG. 2E is a side view of one of the electrodes 212 of the electrode array 210 shown in FIG. 2A. Each electrode 212 of the electrode array 210 consists of a tip 216 and a shaft 220, as illustrated in FIG. 2E. The electrode can be fabricated to any length. Typically, the electrode is 20 mm in length. The electrode array may be fabricated so that all of the electrodes are of the same length. Alternatively, the electrodes may be graded so that there are variations in the electrodes per row of electrodes. The electrodes may also vary across the entire electrode array so each electrode may or may not have the same length as the neighboring electrodes. As previously mentioned, the electrode 212 can be designed and fabricated such that the entire electrode has a shape that tapers toward the tip 216 of the electrode to facilitate insertion of the electrode into the tissue. Alternatively, only the tip of the electrode is tapered, as is illustrated in FIG. 2E. The electrode tip 216 is typically made out of a conductive material or a material that has a low resistance, such as a conductive metal. The material is also preferably inert with respect to the tissue that it comes in contact with. Examples of materials that may be used for the electrode include, but are not limited to, platinum, gold, iron oxide, tungsten, aluminum, stainless steel, or gold.

Figure 2F:
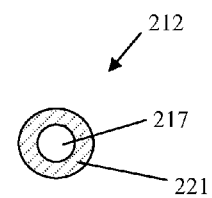
Figure 2G:
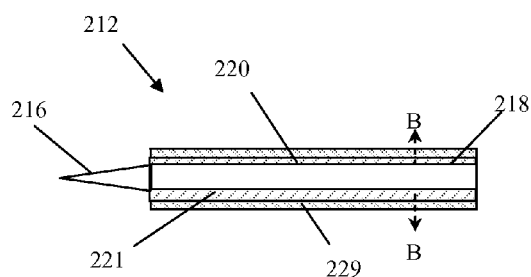
Figure 2H:
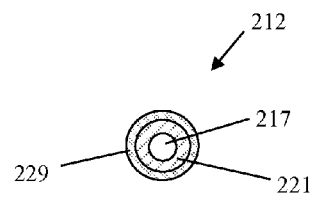

It is known in the art that electrodes that record from cells are designed such that only the minimum required amount of conductive material is exposed to the tissue whereas the rest of the electrode is covered in an electrical insulating material. The portion of the electrode that is exposed needs to be insulated in order to reduce the ambient noise detected by the electrodes from the surroundings as well as noise due to adjacent electrodes. The electrical device described herein typically has electrodes 212 in which 1 mm of conductive material is exposed outside the insulation 221, which forms the tip 216 of the electrode 212. The shaft 220 of the electrode 212, as shown in FIG. 2B, typically comprises the remainder of the electrode 212. The shaft 220 of the electrode 212 can be coated with any suitable electrical insulating material including, but not limited to, silicon dioxide, Teflon® (polytetrafluoroethylene), silicone nitride, epoxy resins, polyamides, or any other suitable biocompatible polymer that is inert with respect to the tissue the material comes in contact with. In a further embodiment, the electrode, once coated with an insulating material can be further coated with a metallic layer that will serve as a ground for the electrode and insulate RF signals from the shaft. The insulating material can be of a uniform thickness along the entire length of the electrode or alternatively will thin along the shaft of the electrode with the thickest portion of the insulating material being at the base of the electrodes and the thinnest portion of insulating material being at the tip of the electrode. FIG. 2F illustrates a cross section of the electrode 212 shown in FIG. 2E depicting the conductive portion 217 of the electrode 212 surrounded by an insulating layer 221. The electrodes shown in FIGS. 2E and 2F are typically coated with an outermost conductive layer 229, as shown in FIGS. 2G and 2H, where FIG. 2G is a lateral cross-section of an electrode coated with an insulating layer and further coated with a conductive layer, and FIG. 2H is a cross section of FIG. 2G along B-B, near the base of the electrode. In such an embodiment, both the center portion and the outermost layer of the electrode are conductive. The outermost layer 229 is electrically grounded. This ensures that the shaft portion of the electrode will neither emit any electrical RF energy nor pick up a response from the sample. These two conductive portions, 217 and 229, are separated by a layer of insulating material 221, to form an electrode in electrical communication with a co-axial cable to isolate RF signals only from the tip. In such a configuration, the signal to noise ratio is further improved because such a configuration allows the signal to be emitted and collected from the tip of the electrode and not from the shaft of the electrode thereby ensuring a highly localized measurement volume of sample located near the electrode tips.

Figure 3:
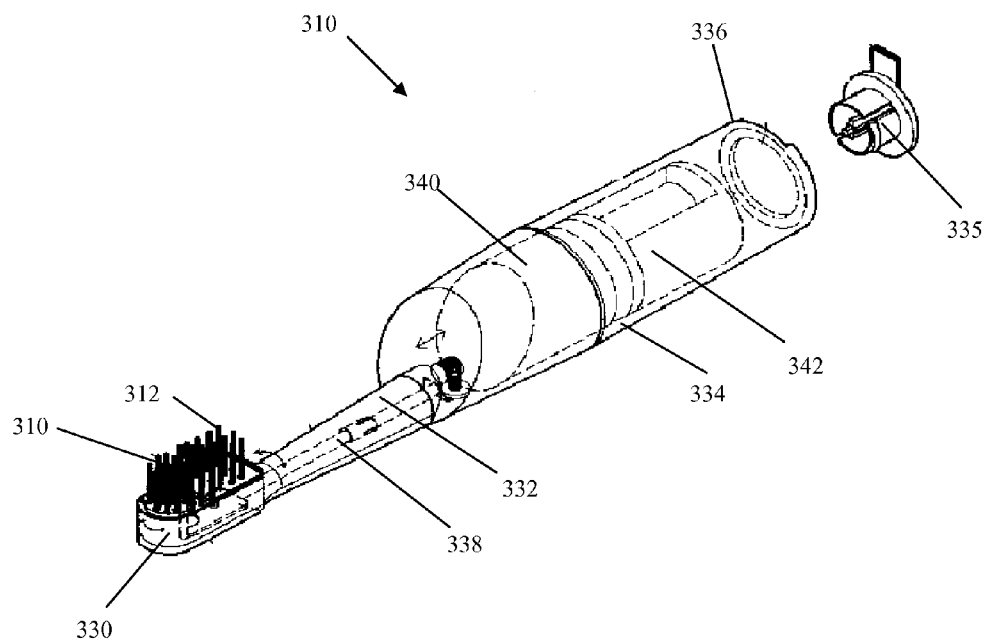
FIG. 3 illustrates a perspective view of a handheld electrical system with probe head.

Although the electrode array can be used alone by placing the electrode array directly in the tissue to be diagnosed or probed, it may be beneficial to integrate the electrode array 310 into a handheld device 300 as shown in FIG. 3. The electrode array 310 can be directly attached to the handheld device 300. Alternatively, the electrode array 310 can be part of a probe head 330 that is attached to the handheld device 300 as seen in FIG. 3. The probe head 330 can be configured to the optimal size for the sample or for the abnormal tissue or cells. In FIG. 3 the electrode array 310 and probe head 330 are attached to the handle 334 of the device 300 by the neck 332. The probe head 330 can be permanently attached to the handheld device 300. In such a configuration, the entire device 300 can be disposed of in its entirety. Alternatively, the electrode array 310 can be cleaned and sterilized and then reused. Alternatively the handle 334 and the neck 332 of the device 300 are reusable while the probe head 310 is disposable. The probe head 310 can also be attached to the neck 332 of the device 300 permanently and the probe head 310 and neck 332 of the device 300 together are disposable, whereas the handle 334 of the device 300 is reusable.

When in use, the user handles the handle 334 of device 300 and approaches the tissue with the probe head 330, so that the electrodes 312 of the electrode array 310 come in contact with the sample. Typically, the handheld device 300 is configured so that the probe head 330 is rotatable with respect to the handle 334 to facilitate the positioning of the electrodes in the sample. Further, the neck 332 of the handheld device 300 is typically translatable with respect to the handle 334. The probe head 330 can then be translated either closer to, or further from, the handle 334 of the device 300, or distal to or proximal to the sample while the handle 334 portion of the device 300 remains stationary.

Once the probe head 330 with electrode array 310 has been connected to the handle 334 of the device 300, the wires 338 connected to each electrode 312 of the electrode array 310 are typically fed through the neck 332 of the device 300 to a multiplexer 340 in communication with a signal generator 342. The multiplexer can be housed within the handle 334 of the device 300 and be in communication with an external signal generator. Alternatively, both the multiplexer 340 and the signal generator 342 are both housed within the handle 334 of the device 300. The signal generator 342 and the multiplexer 340 of the device 300 can be power by an external power cord or alternatively the handheld device can be powered by a battery 335, as shown in FIG. 3, which can be replaced by exchanging the used battery with a new battery or which is a rechargeable battery which can then be recharged.

The handheld device stimulates and records the signals generated by the cells of the sample that it comes in contact with. The signals or data generated by the handheld device, when detected and recorded, can be directly transferred to an external processor for analysis or data storage. The data can be transferred directly by a cable attached to the device base 335. Alternatively, the handheld device is equipped with a wireless interface, so that the signal is transferred to the computer through a wireless interface. Another method for transferring data from the device to a computer is to outfit the handheld device 300 with a processor capable of storing the signals that it detects and which can then later be connected to the computer to transfer the data. The device 300 can be plugged into the computer through a USB cable or can be docked to a unit that transfers the data to the computer.

Figure 4A:
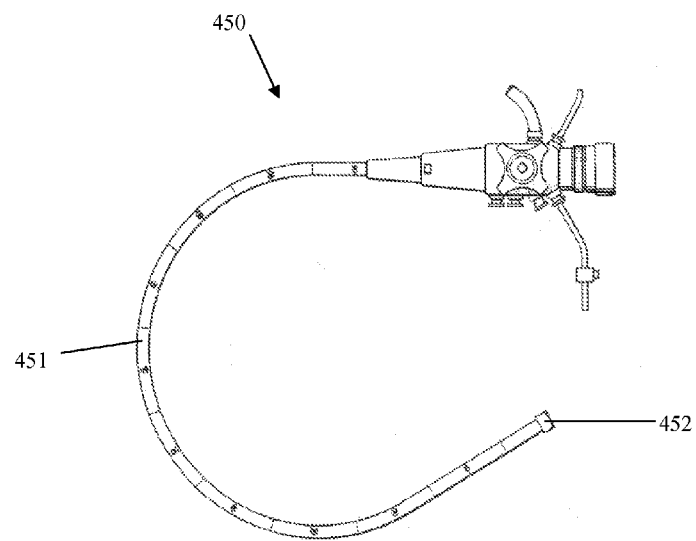
FIG. 4A illustrates one embodiment of an endoscope.
Figure 4B:
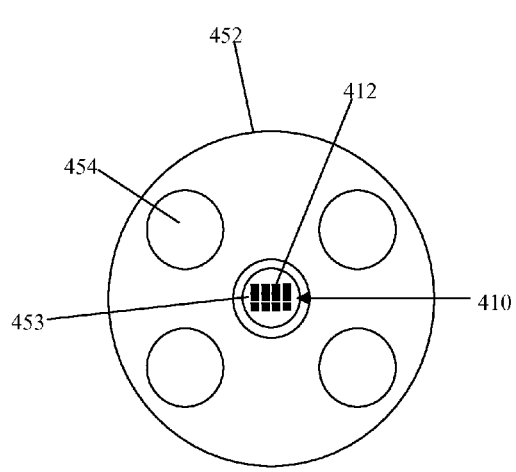
FIG. 4B illustrates a 5-bore endoscope with the electrical device.

The electrode array can be used in a handheld unit as previously described. Alternatively a modified version of the electrode array can be incorporated into other medical devices. For example, an electrode array can be incorporated into an endoscope. An exemplary illustration of an endoscope 450 is shown in FIG. 4A. Before the tube 451 of the endoscope 450 is introduced into the patient, the end 452 of the endoscope 450 is outfitted with an electrode array 410. FIG. 4B illustrates the end 452 of a 5-bore endoscope 450 as viewed from the front. When used together with an endoscope 450, a wireless electrode array (400 in FIG. 4C) can be inserted into one of the bores 453 of the endoscope 450. In FIG. 4B, as indicated by the electrodes 412 of the electrode array 410, the device 400 has been inserted into the center bore 453 of the endoscope. The remaining bores 454 remain available for the introduction of other implements. It can be appreciated that the device 400 does not have to be inserted into the center bore 453 but can be inserted into any of the remaining bores 454. Additionally, although only one device 400 has been inserted into one of the bores, like the center bore 453 of FIG. 4B, more than one device 400 can be simultaneously be inserted into any of the remaining bores 454 and used together.

Figure 4C:
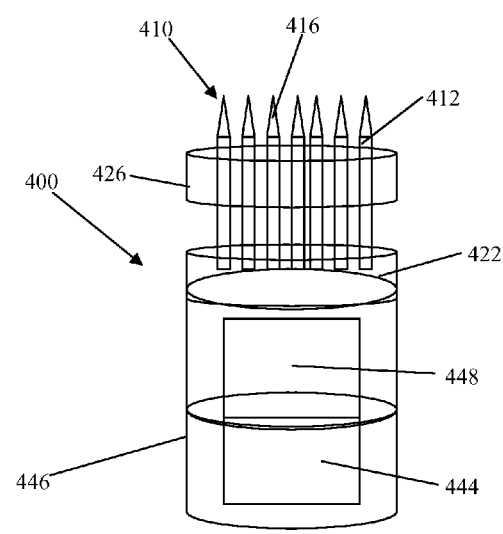
FIG. 4C illustrates an isolated electrical device.

A more detailed view of a wireless device 400 is shown in FIG. 4C. As seen in FIG. 4C, the wireless device 400 consists of an electrode array 410 with a number of electrodes 412 fabricated on a fixed base 422. In the embodiment shown in FIG. 4C, the wireless device 400 is further outfitted with a moving plate 426 used to guide the level of insertion of the electrode tips 416 and whatever portion of the electrodes 212 of the electrode array 410 are desired to be inserted into the tissue. The fixed plate 422 of the device 400 shown in FIG. 4C is in electrical communication with the housing 446 of the device 400. The housing 446 in this embodiment contains an electrical circuit 448 and a wired or wireless interface 444. The electrical circuit typically consists of at least a multiplexer and a signal generator. The housing 446 of the device 400 is then inserted into one of the bores, like the device 400 inserted into the center bore 453 of the endoscope shown in FIG. 4B. The electrodes 412 of the electrode array 410 extend past the surface of the end 452 of the endoscope 450.

Figure 5:
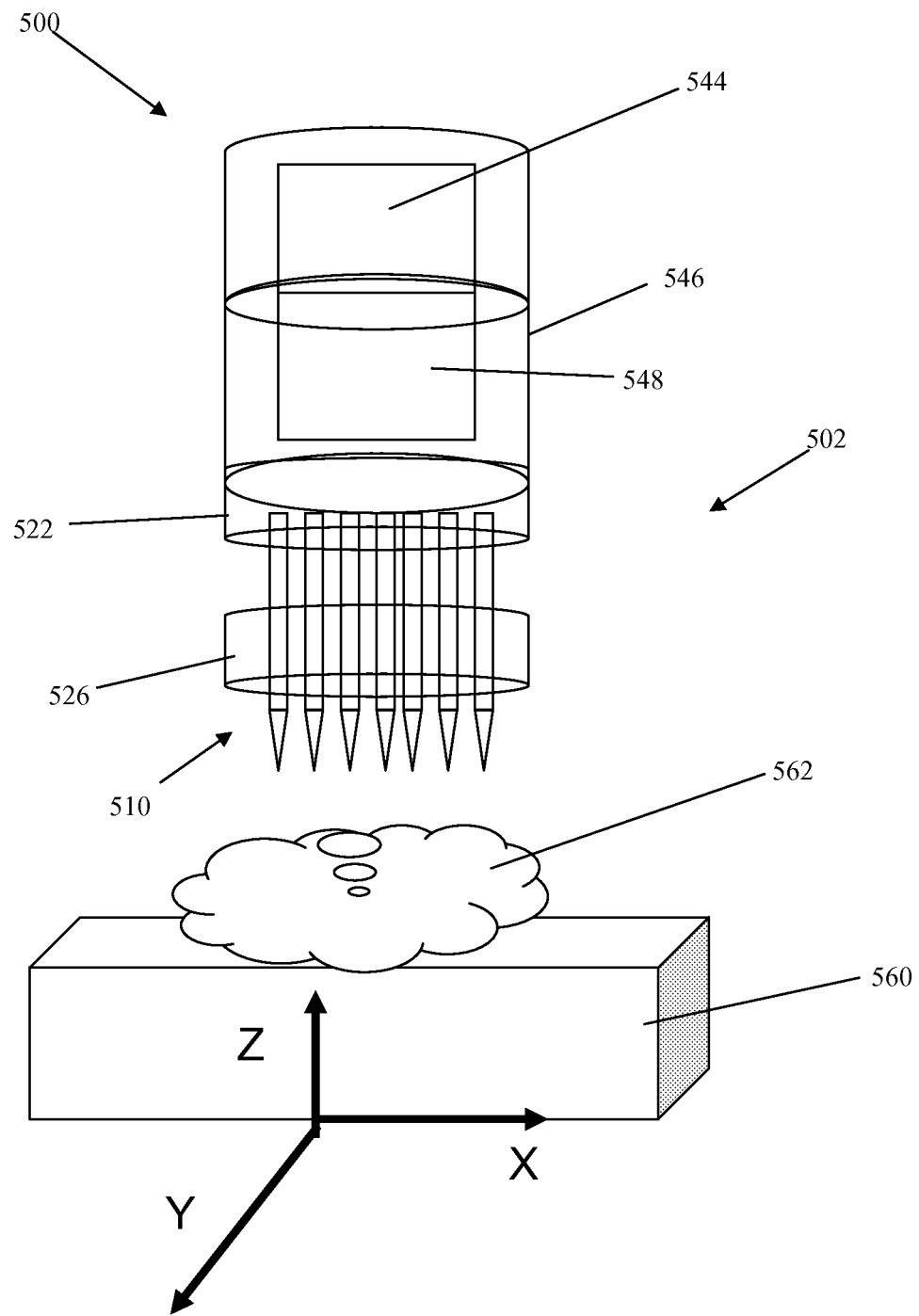
FIG. 5 illustrates the electrical device as used in a metrology apparatus.

The device 500 described herein in some embodiments is further used as part of a metrology apparatus 502 as shown in FIG. 5. The metrology apparatus 502 consists of a motorized stage 560 which can be used to scan a sample 562 in three dimensions. A sample 562 is placed on the motorized stage 560 either directly or as a slide preparation and measurements will be made to the sample 562 through an automated system (not shown). The whole sample 562 can be scanned or alternatively the user can identify and define the regions of the sample 562 to be scanned and input these regions into the automated system with a user interface software program. The boundaries of the sample are typically determined optically or by a specific hardware limiter that the operator will input to the automated system. The system then registers the exact coordinates to be measured and will associate the measurements with the 3D coordinates of the sample. Once the coordinates have been inputted, the device 500 is typically fixed to the metrology apparatus 502. The sample 562 is then translated in XYZ direction using the motorized stage 560 through the software control. The spatially resolved results are then mapped into the sample coordinates using a stage control location encoders. The 3D results of the sample scan are then displayed on the system monitor. If present, "care areas" of malignant cell response will be highlighted compared to benign regions. The data gathered is then statistically tested and compared with a benign reference response for the specific sample. Deviations outside the normal distribution band will be highlighted. Based on the 3D image and the observed margins the surgeon will decide if the extracted sample was adequate or if more tissue is to be extracted and from which location. Repeat measurements on the 2nd sample extracted will be carried in a similar way to assure clean margins.

Figure 6:
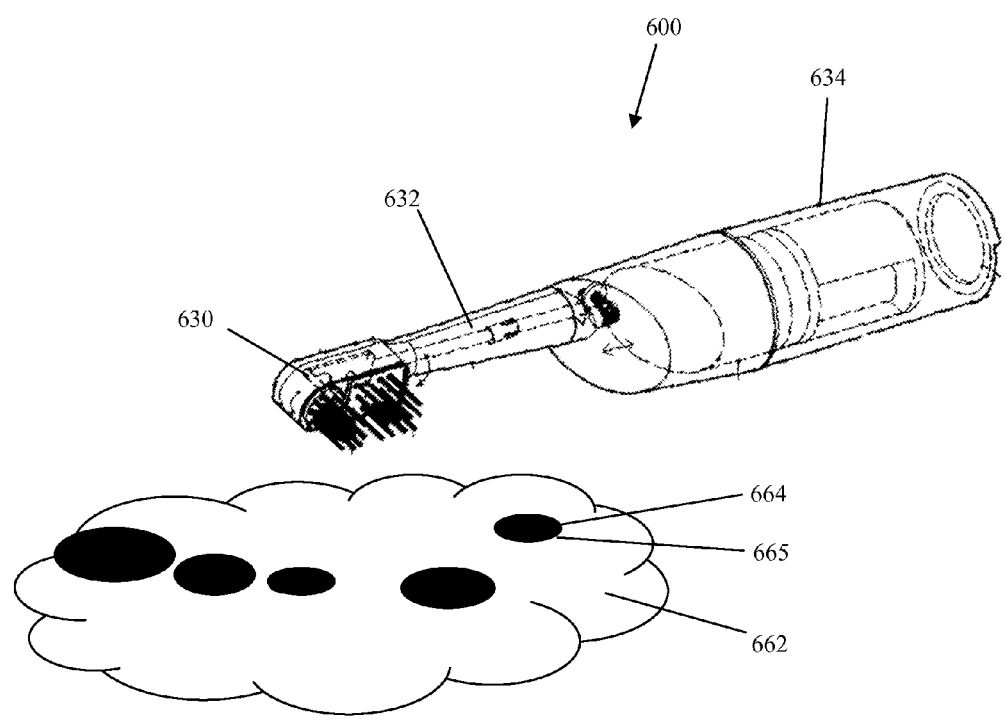
FIG. 6 illustrates the probe head of the electrical system as used in an in-situ setup.

The device can be used in vivo, in the body, in vitro, in isolated cells, or in situ, detecting abnormalities in removed intact tissue. FIG. 6 illustrates the device 600 as used in situ. As in other methods of use, a suitable probe head 630 with an electrode array 610 is attached to the handle 634 of the device 600 by the neck 632. A tissue sample 662 with areas of interest 664 is removed from the subject. The user then uses the handle 634 to direct the electrodes 612 to the areas of tissue 662 to be sampled. The device 600 emits and detects signals that designate the locations of the areas of interest 664 as the tissue 662 is probed and establishes the margins 665 of the areas of interest 664. These areas of interest 665 can are then mapped in relation to the tissue 662.

Figure 7:
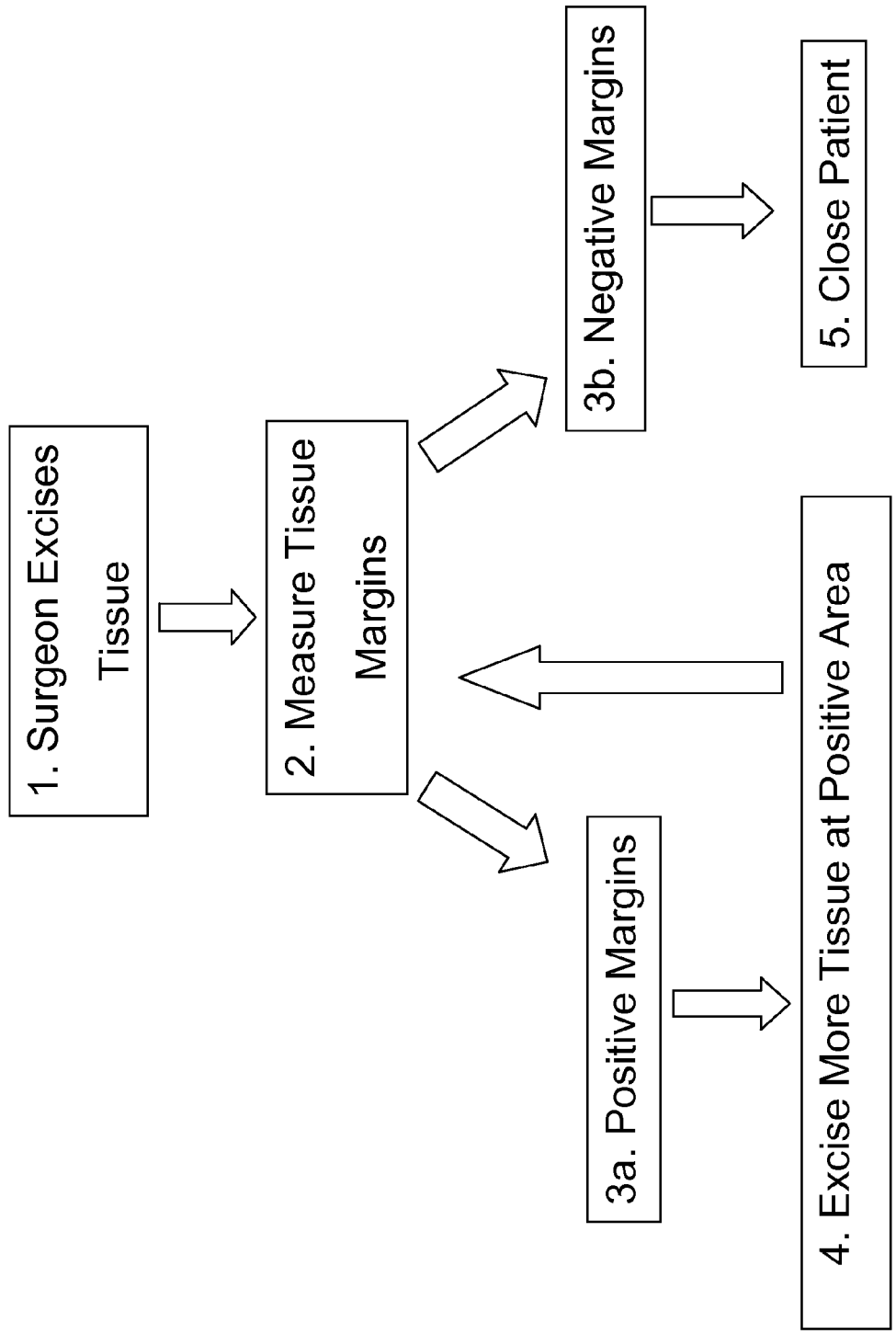
FIG. 7 is a block diagram of the steps for using the electrical system.

In addition to being used to diagnose a cancerous condition by detecting abnormalities in cells, the electrical device measured herein can be used in the operating room by a surgeon in real-time to ensure complete removal of abnormal tissue, such as cancer cells, during a surgical procedure. FIG. 7 illustrates a flow diagram of how the device may be used to ensure removal of problematic tissue. When a patient has been diagnosed with cancer, the patient undergoes surgery to remove the tissue. Once the surgeon has gained access to the cancerous tissue, the surgeon excises the tissue from the patient. The tissue margins are then measured to detect whether the entire cancerous area has been excised. If the device indicates that the entire cancerous region has not been excised, more tissue is excised and the margins of the tissue measured again. This is repeated until the margins of the tissue excised indicate that the cancerous tissue has been excised in its entirety. The surgeon can then close the site of the surgical incision knowing that the cancerous tissue has been completely removed.

II. KITS

Kits employing the devices, components and materials of the invention can also be employed. A variety of kits are also contemplated. For example, a kit for diagnosing a biological tissue can comprise, for example, a probe and a probe head adapted and configured for use with the probe, the probe head comprising at least a plurality of electrode elements in an array adapted apply an electrical signal to a biological tissue. Additionally, the kit may include an electrode selector adapted to switch between the electrode elements. Furthermore, the kit could include a plurality of probe heads connectable to the probe. The kit including an embodiment of the invention described previously in some instances further includes a console component. The console typically consists of a processor and some kind of display unit, such as a computer and a monitor. The console can be directly linked to the device. Alternatively the console can be connected to a base. When a base is included in the kit, the device is linked to the base. The device can be linked to the base through a hard-wired connection. Alternatively, the device can be linked to the base through a wireless connection. The wireless connection is typically an approved wireless connection that uses a hospital approved frequency and bandwidth. The properties detected by the device are then typically displayed on the console.

III. METHODS

A variety of methods are also contemplated. One method includes a method of diagnosing a biological sample in real-time. The method comprises: engaging a biological tissue with a probe, having a probe head distally connectable to the probe, the probe head further comprising at least a plurality of electrode elements in an array for applying an electrical signal to the biological tissue of a mammal; an RF signal source for applying the electrical signal to the electrode array; an electrode selector adapted and configured to switch the electrical signal from the RF signal source between the plurality of electrode elements; and a detection circuit for analyzing a dielectric signal received from the biological tissue; emitting an electrical signal from one or more electrode elements; collecting a dielectric signal from the biological sample; analyzing the dielectric signal received from the biological tissue to produce a result; and diagnosing the biological sample based on the result. The method can further comprise engaging the biological by applying the probe to a tissue site within the body of the mammal. Alternatively, the method can further comprise engaging the biological sample by approaching the tissue site within the body of the mammal with the probe. Additionally, the probe can be inserted into the body of the mammal through an endoscope. The probe head can be replaced, if desired, with a second probe head. The second probe head can then emit an electrical signal, collect a second dielectric signal from the biological sample, analyze the second dielectric signal received from the biological sample to produce a result, and thereby diagnose the biological sample based on the result. Furthermore the first electrical signal and the second electrical signal are the same. Alternatively, the method can further comprise a step of analyzing the signal in real-time. Further, the signal received from the biological sample to a signal from a reference sample. For example, the reference sample can be a benign tissue sample, the benign tissue sample having been obtained from the same mammal

IV. EXAMPLES

Example 1

Intra-Operative Assessment in Breast Conservation Surgery

Experiments were conducted using three prophylactic mastectomy fixated tissue samples. The samples were pre-diagnosed with either invasive carcinoma, ductal carcinoma in situ (DCIS), or benign tissue. Measurements were obtained using the electrical device described herein. Measurements were made at several locations including transition areas between malignant and benign tissue to assess sensitivity and resolution of margins detection. In the tissue sample from one patient, measurements indicated that the entire sample was a benign tissue sample. The sample showed a large frequency spread in frequency response typical to benign tissue. The electrical device was able to differentiate the benign tissue and margins from cancerous and fibrous tissue is a sample from a second patient. The tissue showed electrical responses about 100 times lower than responses from benign tissue.

Example 2

Detection of Breast Cancer in vitro

The electrical device can be used to detect suspect areas of tissue during a lumpectomy. Once the surgeon excises the suspect breast tissue, either the surgeon, a pathologist, or lab technician in the operating room can use the handheld device as shown in FIG. 3 to investigate if the margins of the tissue are free of malignant tissue, the steps of which are shown in the FIG. 7. The user approaches the tissue with the handheld device and inserts the electrode array into the tissue at the desired location. The user than uses the device to detect and measure the electrical response from the suspected areas of tissue. A reference signal specific to the patient is collected from a clear benign portion of the tissue and the results of the benign tissue response are compared to the measurements obtained from the suspect portions of the sample. Cancerous tissue has been shown to exhibit lower resistance and higher capacitance as compared to benign tissue. The impedance vector magnitude and angle will be used to determine if the tissue is malignant or benign. If it is determined that the suspect tissue is malignant tissue, the surgeon can follow up with excision of more tissue in the suspected area in the body. The newly excised tissue is then measured again in vitro to assure the margins are clear before closing the patient. If the margins are clear, the surgeon can then close the patient.

Example 3

Detection of Breast Cancer In Vivo

The electrical device can also be used to detect cancerous tissue in vivo during a lumpectomy. During the lumpectomy, the surgeon will use the probe in the body cavity of the patient to assess if, once the suspect tissue has been excised, the remaining tissue in the breast is free of malignancy. Once the excision procedure is complete, the surgeon will use the device inside the body to scan the surface of the cavity. The depth of the electrode will be adjusted based on the surgeon and hospital convention and the assigned depth will be measured using the probe. The results obtained from a benign tissue sample will be registered to form a baseline for the patient tissue response and the results from the suspect areas will be compared with the benign values. The console will display the variations in the tissue response. If a larger deviation is observed in the impedance vector, or resistance, and/or capacitance compared to the benign signals, the surgeon will then note the area and will excise more tissue at the margins to ensure complete excision of the cancerous tissue before closing the patient.

Example 4

Sentinal and Lymph Node Detection and Excision

As part of a typical cancer excision surgery the surgeons sometimes excise sentinal lymph nodes and additional nodal areas to determine whether the cancer has metastasized. The electrical probe can be used in vivo, to make sure that the node is cancer free before excising it. Additionally the device can be used in-vitro to find out if more lymph nodes need to be excised before the patient is closed.

Example 5

In Situ Prostate Cancer Biopsy

Current methods for conducting a prostate cancer biopsy include taking tissue from 12 random sites in the prostate gland. The tissue taken during the biopsy is then sent to a lab and the results are obtained a few days later. If the areas of cancer are not within one of the 12 random sites, the procedure needs to be repeated again. Using the electrical device described herein, in conducting a prostate cancer biopsy, the electrical probe of the invention can be mounted in an endoscope and the organ suspected of cancer can be electrically tested using the probe. The response can then be compared to the response from a benign area of the organ. If a noticeable deviation from the benign tissue response is detected, the surgeon will excise the tissue from this area to perform a permanent pathology.

Example 6

Electrical Biopsy

The invention also can be used in a biopsy to determine whether a suspected area of tissue is malignant or not. Because the device operates in real time, the invention can help reduce the amount of benign biopsy procedures done today as well as reduce the cost of these procedures. It is found that more than 80% of biopsies result in the sample being benign tissue, therefore the device will be able to reduce the cost of these procedures to those tissue portions that are more likely to show malignancy.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of diagnosing a biological tissue comprising:
   placing the biological tissue on a stage of a metrology unit;
   engaging the biological tissue with a probe, the probe having a probe head distally connectable to the probe, the probe head further comprising
      a fixed plate having a plurality of electrode elements forming an electrode array extending therefrom, wherein each electrode element further comprises a tip and a shaft and is adapted to be separately actuable to apply an electrical signal to the biological tissue of a mammal between selected pairs of electrode elements on the electrode array wherein each of the one or more pairs of electrode elements form an electrical circuit through the biological tissue;
      a moveable plate adjacent the fixed plate wherein the moveable plate controls a depth of penetration of the electrode elements;
      an RF signal source for applying the electrical signal to the electrode array;
      an electrode selector adapted and configured to switch a signal pulse from the RF signal source between the plurality of electrode elements; and
      a detection circuit for analyzing a dielectric response received from a first electrode element by a second electrode element after the electrical signal passes through the biological tissue;
   emitting an electrical signal from one or more electrode elements in the electrode array of the probe;
   collecting the dielectric response from the first electrode element in the electrode array of the probe by the second electrode element in the electrode array of the probe after the electrical signal passes through the biological tissue.

2. The method of claim 1, further comprising the step of
   replacing the probe head with a second probe head and thereafter emitting an electrical signal;
   collecting a second dielectric response from a first electrode element on the second probe head by a second electrode element on the second probe head after the electrical signal passes through the biological tissue;
   analyzing the second dielectric response received from the first electrode element on the second probe head by the second electrode element on the second probe head after the electrical signal passes through the biological tissue to produce a second result; and
   diagnosing the biological tissue based on the second result.

3. The method of claim 2, wherein the first dielectric response collected by the first probe head and the second dielectric response collected by the second probe head are the same.

4. The method of claim 1, wherein the step of analyzing the signal is performed real-time.

5. The method of claim 1, further comprising the step of comparing the signal received from the first electrode element by the second electrode element after the electrical signal passes through the biological tissue to a signal of a reference sample.

6. The method of claim 5, wherein the reference sample is a benign tissue sample.

7. The method of claim 6, wherein the benign tissue sample is obtained from the same individual mammal.

8. The method of claim 1, wherein the step of emitting the electrical signal is performed on a first set of electrode elements and the step of collecting the first dielectric response is performed on a second set of electrode elements different than the first set of electrode elements.

9. The method of claim 1, wherein the step of emitting the electrical signal is performed on a first set of electrode elements and the step of collecting the first dielectric response is performed the first set of electrode elements.

10. The method of claim 1, wherein the step of emitting the electrical signal is performed on a first set of electrode elements and the step of collecting the first dielectric response is performed on a second set of electrode elements which includes at least some of the first set of electrode elements.

11. The method of claim 1, wherein the step of emitting the electrical signal is performed on a set of electrode elements on the array that is less than all of the electrode elements on the array.

12. The method of claim 1, further comprising the step of moving the moveable plate relative to the fixed plate to adjust the depth at which the electrode elements penetrate the tissue.

13. The method of claim 1 wherein the dielectric property is measured locally.

14. The method of claim 1 wherein at least one of a near-field response and far-field response is measured.

15. The method of claim 1 wherein the metrology unit scans the sample in three dimensions at different locations.

* * * * *